United States Patent [19]

Courbat et al.

[11] Patent Number: 4,634,718
[45] Date of Patent: Jan. 6, 1987

[54] USE OF O-SUBSTITUTED DERIVATIVES OF (+)-CYANIDAN-3-OL AS COMPOUNDS HAVING IMMUNOMODULATING PROPERTIES

[75] Inventors: Pierre Courbat, Nyon; André Weith, Prangins; Alban Albert, Avully, all of Switzerland

[73] Assignee: Zyma SA, Nyon, Switzerland

[21] Appl. No.: 834,507

[22] Filed: Feb. 28, 1986

Related U.S. Application Data

[63] Continuation of Ser. No. 713,561, Mar. 18, 1985, abandoned, which is a continuation of Ser. No. 531,809, Aug. 25, 1983, abandoned, which is a continuation of Ser. No. 247,961, Mar. 26, 1981, abandoned.

[30] Foreign Application Priority Data

Apr. 3, 1980 [CH] Switzerland ............... 2679/80

[51] Int. Cl.$^4$ ................................................. A61K 31/35
[52] U.S. Cl. ................................................. 514/460
[58] Field of Search .................................... 514/460

[56] References Cited

U.S. PATENT DOCUMENTS 4,248,789  2/1981  Okada .................... 260/345.2

FOREIGN PATENT DOCUMENTS 0003274  8/1979  European Pat. Off. .
2740346  3/1978  Fed. Rep. of Germany .
2345441  3/1977  France .

OTHER PUBLICATIONS

Chem. Abst (vol. 90) (1979)–67141y.
Journal of Biological Modifiers 1, pp. 15–26 (1982).
Int. J. Immunopharmacology 4, pp. 256 (1982).
Int. J. Immunopharmacology 4, pp. 268 (1982).
Int. J. Immunopharmacology 4, pp. 278 (1982).
Drugs of the Future 6, pp. 477 (1981).
Drugs of the Future 9, pp. 629 (1984).

*Primary Examiner*—Stanley J. Friedman
*Attorney, Agent, or Firm*—Michael W. Glynn; Irving M. Fishman

[57] ABSTRACT

The present invention relates to the use of O-substituted derivatives of (+)-cyanidan-3-ol corresponding to the formula

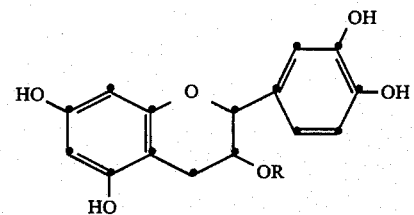

and their addition salts, in which R represents an optionally substituted hydrocarbon radical, an acyl radical of an organic carboxylic acid containing at least 2 carbon atoms, of a carbonic acid, or of an organic sulphonic acid, of a radical of an inorganic acid containing at least one oxygen atom, as compounds having immunomodulating properties, and pharmaceutical compositions for this purpose.

2 Claims, No Drawings

USE OF O-SUBSTITUTED DERIVATIVES OF (+)-CYANIDAN-3-OL AS COMPOUNDS HAVING IMMUNOMODULATING PROPERTIES

This application is a continuation of application Ser. No. 713,561, filed Mar. 18, 1985 which is a continuation of Ser. No. 531,809, filed Aug. 25, 1983, which is a continuation of Ser. No. 247,961 filed Mar. 26, 1981, all abandoned.

The present invention relates to the use of O-substituted derivatives of (+)-cyanidan-3-ol as compounds having immunomodulating properties, and pharmaceutical compositions for this purpose.

It has been found that O-substituted derivatives of (+)-cyanidan-3-ol, especially 3-O-substituted derivatives of (+)-cyanidanol corresponding to the formula I

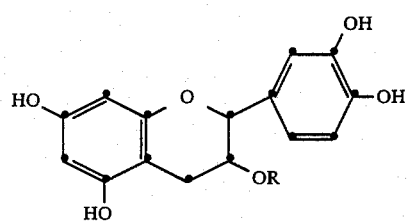

and their addition salts, in which R represents an optionally substituted hydrocarbon radical, an acyl radical of an organic carboxylic acid containing at least two carbon atoms, of a carbonic acid or of an organic sulphonic acid, or a radical of an inorganic acid containing at least one oxygen atom, have immunomodulating properties which are clearly advantageous for the treatment of illnesses involving a change in immune response of the organism, such as all recurrent or prolonged viral diseases, such as, for example, recurrent herpes, or for the treatment of illnesses in the course of which stimulation of the organisms defences permits healing or an improvement in the condition of the patient, and especially viral, bacterial or parasitic diseases, cancer diseases and all auto-immune disorders such as, for example, rheumatoid polyarthritis.

Thus, for example, the compounds are clearly advantageous for the treatment of various malignant tumours. They are substances having both increased anti-tumour activity and reduced side-effects. The active ingredient of these novel products is a biocatalyst that does not belong to the group of conventional anti-tumour derivatives. In fact, if these substances have a direct cytotoxic activity on tumour cells they also have immunomodulating properties detected in vivo not only in neoplastic models but also as a result of standard immunological studies. Thus, the fundamental value of these compounds in fighting cancer rests on their selective toxicity for cancer cells as opposed to normal cells and on their ability to increase the organism's defence potential.

For example, these substances have been successfully subjected to the tests of the National Cancer Institute, U.S.A. The tests involved a very comprehensive screening programme using the leukaemic system P388 in mice. Treatments (acute or chronic) with the compounds have a direct cytotoxic effect on these leukaemic cells. To complete this series of tests, two ascitic tumours, sarcoma 180 in mice and hepatoma AH13 in rats, were also used as models to demonstrate the direct anti-tumour effects of the compounds. A dose of 250 mg/kg of drug administered for 5 days to the mice and rats is sufficient to prolong life to a significant extent compared with the control groups and a dose of 500 mg/kg even ensures more than 30 days' survival in the case of 80 % of the animals.

These anti-tumour compounds also have an immunomodulating activity tested in numerous neoplastic models.

Thus, leukaemia L1210 Ha according to three types of experiment on mice permits the detection of these valuable immunomodulating properties; for example, isogenous CD2F1 mice are treated on day 0 with $10^7$ irradiated L1210 Ha cells and inoculated on the 14th day with various quantities of living cells having the same isogenous leukaemia. The effect of the compounds is demonstrated by the increase in the duration of life and by the greater number of survivors at 30 days.

In addition, CD2F1 mice are inoculated with $10^5$ L1210 Ha cells and injected on the following day with $10^7$ irradiated tumour cells. The said compounds are administered to the mice before and after inoculation. The effect of these substances is very positive, prolonging life and increasing the number of survivors at 60 days. Furthermore, complementary effects on animals immunodepressed beforehand with doses of 150 mg/kg of cyclophosphamide confirm the effect observed after treatment with these compounds, showing that the reactivity of the animals was intact.

Finally, CD2F1 mice to which 10 L1210 Ha cells had been transplanted and which were then treated the following day with adriamycin, provide the same conclusions on the beneficial action of these compounds.

The compounds have a beneficial action not only on ascitic tumours and on leukaemia but also on a solid tumour, the Lewis Lung carcinoma (3LL) in mice. This neoplastic model is considered according to the E.O.R.T.C. to reproduce human tumours best. The substances have significant positive results in three series of studies. The compounds are administered for 10 days to C57B1/6 mice infected with the isogenous tumour 3LL. They are also administered subsequently in a Methyl CCNU treatment at the rate of 10 mg/kg to animals having tumours. They also limit the development of metastases when the primary tumour has been removed by surgery.

The compounds have an immunostimulating activity. In tests in vivo they have shown their pharmaceutical potential which is such as to increase the cytotoxic capacity of purified macrophages with respect to cancer cells. These macrophages, the capacities of which have been considerably increased by these products, are considered to play a major role both in anti-tumour resistance and in the control of immunological reactivity.

Finally, the compounds have established definitively their therapeutic potential by showing beyond doubt their positive effect in the production of antibodies in non-neoplastic conditions, which proves that the effect of these products is in fact the result of the reactivity of the host.

When CD2F1 mice are injected with $10^8$ sheep erythrocytes (SRBC) or with 0.5 µg of pneumococcus polysaccharide s.III, the number of splenocytes capable of producing specific antibodies is increased decisively, as can be proved by the haemolytic plaque test on gel according to Jerne and Nordin. The antibodies are measured by the response peaks, with single and/or repeated injections of these products.

The compounds of the formula I and their addition salts are described in European Patent Application No. 78 810024.6 and in the corresponding applications in other countries claiming the Swiss priority of 25th November 1977. According to these patent applications they possess a pharmacological activity in the prevention of hepatonecrosis and also inhibit lipoperoxidation. They can also act on collagen fibrillation and inhibit the degradation of collagen as well as activity of lysosomal enzymes while at the same time increasing the stability of the membranes of the lysosomes.

In the compounds of the formula I, the radical R may have the following meanings:

An optionally substituted hydrocarbon radical is, for example, an aliphatic, cycloaliphatic, cycloaliphatic-aliphatic, aromatic, aromatic-aliphatic, heterocyclic or heterocyclic-aliphatic hydrocarbon radical. These radicals may be substituted and they contain from 1 to 24 carbon atoms.

An acyl radical of a carboxylic acid is especially the radical of an aliphatic, cycloaliphatic, cycloaliphatic-aliphatic, aromatic, aromatic-aliphatic, heterocyclic or heterocyclic-aliphatic acid, optionally substituted and containing from 2 to 24 carbon atoms.

A radical of a carbonic acid is, for example, a radical of esterified or amidated carbonic acid.

A radical of an organic sulphonic acid is especially the radical of an aliphatic, aromatic or aromatic-aliphatic sulphonic acid, optionally substituted and containing from 1 to 12 carbon atoms.

A radical of an inorganic acid is especially the radical of an acid having as the central atom an atom from one of the groups III, IV, V or VI of Mendeleev's periodic table and especially from periods 1 and 2. Examples of central atoms that should be mentioned are sulphur, phosphorus, boron and nitrogen.

An aliphatic hydrocarbon radical is especially a saturated hydrocarbon radical, such as an alkyl radical, or an unsaturated hydrocarbon radical, such as an alkenyl or alkynyl radical. They may be linear or branched. Such radicals may, in appropriate cases, be mono-substituted, di-substituted or poly-substituted by functional groups.

An optionally substituted cycloaliphatic or cycloaliphatic-aliphatic hydrocarbon radical is, for example, a monocyclic, bicyclic or polycyclic cycloalkyl or cycloalkenyl group, or a cycloalkyl-lower alkyl, cycloalkenyl-lower alkyl or -lower alkenyl group in which a cycloalkyl radical contains, for example, up to 12, for example 3 to 8 and preferably from 3 to 6, ring carbon atoms, while a cycloalkenyl radical contains, for example, up to 12, for example from 3 to 8 and preferably 5 or 6, ring carbon atoms as well as one or two double bonds, while the aliphatic moiety of a cycloaliphatic-aliphatic radical may contain, for example, up to 7, preferably up to 4, carbon atoms. The above cycloaliphatic or cycloaliphatic-aliphatic radicals may, if desired, be mono-substituted, di-substituted or poly-substituted.

An optionally substituted aromatic hydrocarbon radical is, for example, a monocyclic, bicyclic or polycyclic aromatic hydrocarbon radical, especially a phenyl radical, or alternatively a naphthyl radical, which may, in appropriate cases, be mono-substituted, di-substituted or polysubstituted.

An optionally substituted aromatic-aliphatic hydrocarbon radical is, for example, an optionally substituted aliphatic hydrocarbon radical having up to three optionally substituted monocyclic, bicyclic or polycyclic aromatic hydrocarbon radicals and represents, especially, a phenyl-lower alkyl radical, or alternatively a phenyl-lower alkenyl radical or a phenyl-lower alkynyl radical, it being possible for such radicals to contain, for example, from 1 to 3 phenyl groups and, in appropriate cases, to be mono-substituted, di-substituted or poly-substituted in the aromatic and/or aliphatic moiety.

A heterocyclic radical is especially a monocyclic radical but may also be a bicyclic or polycyclic radical, preferably a saturated or unsaturated aza-, thia-, oxa-, thiaza-, oxaza- or diaza-cyclic radical, for example of aromatic character, having preferably from 2 to 7 carbon atoms and which may, in appropriate cases, be mono-substituted, di-substituted or poly-substituted. The aliphatic moiety in a heterocyclic-aliphatic radical may, for example, have the meaning given for the corresponding aliphatic, cycloaliphatic-aliphatic or aromatic-aliphatic radicals.

The acyl radicals R of an aliphatic carboxylic acid are especially radicals of alkanecarboxylic acids, especially of lower alkanecarboxylic acids, or alternatively of alkenecarboxylic acids, especially lower alkenecarboxylic acids, and also of lower alkanedicarboxylic acids or lower alkenedicarboxylic acids.

The acyl radicals R of a cycloaliphatic, cycloaliphatic-aliphatic, aromatic, aromatic-aliphatic, heterocyclic or heterocyclic-aliphatic carboxylic acid have, in the ring and/or the aliphatic radical, the meanings given above for the cycloaliphatic, aromatic or heterocyclic radicals or the corresponding aliphatic radicals. They may carry substituents.

The acyl radicals R of an esterified or amidated carbonic acid are especially the aliphatic, aromatic or araliphatic esters of carbonic acid, such as a lower alkoxycarbonyl, aryloxycarbonyl or aryl lower alkoxycarbonyl group, or of a carbamic acid preferably mono- or di-substituted by aliphatic, aromatic or araliphatic radicals.

The functional groups appearing as complementary substituents of one of the above-mentioned radicals are, for example, free, etherified or esterified hydroxy or mercapto groups, such as lower alkoxy, lower alkenyloxy or lower alkylmercapto groups, or optionally substituted phenylmercapto groups or phenyl-lower alkylmercapto groups, lower alkoxycarbonyloxy groups or lower alkanoyloxy groups, and also halogen atoms and nitro groups, optionally substituted amino groups, acyl groups, such as lower alkanoyl groups, or optionally functionally modified carboxy groups, such as lower alkoxycarbonyl groups, optionally N-substituted carbamoyl groups, or nitrile groups. The aromatic and heterocyclic radicals may also carry alkyl radicals, preferably lower alkyl radicals, as substituents.

Etherified hydroxy groups should be understood as meaning especially lower alkoxy groups, or alternatively substituted lower alkoxy groups, such as halo-lower alkoxy groups, and also lower alkenyloxy groups, lower alkylenedioxy groups, cycloalkoxy groups, phenoxy groups, phenyl-lower alkoxy groups, or lower alkoxy groups substituted by monocyclic mono-aza-, mono-oxa- or mono-thia-cyclic groups of aromatic character, such as pyridyl-lower alkoxy, furyl-lower alkoxy or thienyl-lower alkoxy groups.

Etherified mercapto groups that should be mentioned are lower alkylmercapto, phenylmercapto or phenyl-lower alkylmercapto groups.

Esterified hydroxy groups are especially halogen atoms or alternatively lower alkanoyloxy groups.

Substituted amino groups are mono- or di-substituted amino groups in which the substituents represent especially optionally substituted monovalent or bivalent aliphatic, cycloaliphatic, cycloaliphatic-aliphatic, aromatic or araliphatic hydrocarbon radicals but also acyl groups. Such amino groups are especially lower alkylamino groups, or di-lower alkylamino groups, or lower alkyleneamino groups optionally interrupted by hetero atoms, such as oxygen atoms, sulphur atoms or, in appropriate cases, by nitrogen atoms optionally substituted, for example by lower alkyl groups, and also acylamino groups, especially lower alkanoylamino groups.

Hereinbefore and hereinafter the general names may have the following meanings:

An alkyl radical is preferably a lower alkyl radical, for example a methyl, ethyl, n-propyl, isopropyl, n-butyl, isobutyl, sec.-butyl or tert.-butyl radical, but also a pentyl, isopentyl, n-hexyl, isohexyl, n-heptyl, octyl, nonyl, decyl, undecyl, dodecyl, tricosyl or tetracosyl radical and the isomers thereof, while an alkenyl radical, preferably a lower alkenyl radical, may, for example, be a vinyl, allyl, n-propenyl, isopropenyl, 2- or 3-methallyl or 3-butenyl group and an alkynyl radical may, for example, be a propargyl or 2-butynyl radical.

The substituted aliphatic hydrocarbon radicals preferably contain hydroxy groups, lower alkoxy groups or halogen atoms and are especially hydroxy-lower alkyl or lower alkoxy-lower alkyl radicals in which the hydroxy or lower alkoxy groups are separated preferably by at least two carbon atoms from the oxygen atom carrying a lower aliphatic radical substituted in this manner, such as 2-hydroxyethyl, 2-hydroxypropyl, 3-hydroxypropyl, 2,3-dihydroxypropyl, 2-methoxyethyl, 2-ethoxyethyl, 2-methoxypropyl, 3-methoxypropyl or 3-ethoxypropyl radicals, or alternatively hydroxymethyl radicals.

A cycloalkyl radical is, for example, a cyclopropyl, cyclobutyl, cyclopentyl, cyclohexyl or cycloheptyl radical, or an adamantyl group, and a cycloalkenyl group is, for example, a 2- or 3-cyclopentenyl, 1-, 2- or 3-cyclohexenyl or 3-cycloheptenyl group and also a 2-cyclopropenyl group. A cycloalkyl-lower alkyl radical or a cycloalkyl-lower alkenyl radical is, for example, a cyclopropyl-, cyclopentyl, cyclohexyl- or cycloheptyl-methyl, -1,1- or 1,2-ethyl, -1,1-, -1,2- or -1,3-propyl, -vinyl or -allyl radical, while a cycloalkenyl-lower alkyl or cycloalkenyl-lower alkenyl radical represents, for example, a 1-, 2- or 3-cyclopentenyl-, 1-, 2- or 3-cyclohexenyl- or 1-, 2- or 3-cycloheptenyl-methyl, -1,1- or -1,2-ethyl, -1,1-, -1,2- or 1,3-propyl, -vinyl or -allyl radical.

A naphthyl radical is a 1- or 2-naphthyl radical while a biphenylyl radical is, for example, a 4-biphenylyl radical.

A phenyl-lower alkyl or phenyl-lower alkenyl radical is especially a benzyl radical, or alternatively a 1- or 2-phenylethyl, 1-, 2- or 3-phenylpropyl, diphenylmethyl, trityl, 1- or 2-naphthylmethyl, styryl or cinnamyl radical. A substituted phenyl-lower alkyl radical is especially a benzyl radical that can be mono-, di- or poly-substituted in the phenyl nucleus and in the case of multiple substitution different substituents may be present. The substituents are especially halogen atoms or lower alkyl groups or alternatively lower alkoxy groups or trifluoromethyl groups, while the benzyl radicals in the substituted nucleus contain a substituent, preferably in the paraposition.

The heterocyclic radicals are, for example, monocyclic mono-aza-, mono-thia- or mono-oxa-cyclic radicals of aromatic character, such as pyridyl radicals, for example, 2-pyridyl, 3-pyridyl or 4-pyridyl radicals, thienyl radicals, for example, 2-thienyl radicals, or furyl radicals, for example, 2-furyl radicals, or bicyclic monoazacyclic radicals of aromatic character, such as quinolinyl radicals, for example, 2-quinolinyl or 4-quinolinyl radicals, or isoquinolinyl radicals, for example 1-isoquinolinyl radicals, or monocyclic thiaza- or oxazacyclic radicals of aromatic character as well as diazacyclic radicals of aromatic character, such as oxazolyl, isoxazolyl, thiazolyl or isothiazolyl radicals, and pyrimidinyl radicals. Aliphatic heterocyclic radicals are lower alkyl or lower alkenyl radicals including heterocyclic radicals, especially those indicated above.

The acyl radicals of alkanecarboxylic acids are especially those of propionic, butyric, isobutyric and valeric acid and the higher up to stearic homologues, those of alkanedicarboxylic acids containing, for example, from 2 to 10, preferably from 3 to 6, carbon atoms, or of alkenedicarboxylic acids containing, for example, from 4 to 7 carbon atoms, for example those of 2-methylsuccinic, glutaric, 3-methylglutaric, 3-ethylglutaric, adipic, pimelic, suberic, azelaic or sebacic acid, preferably the malonic and succinic acids. Acyl radicals of unsaturated aliphatic acids that should be mentioned are those of acrylic, propiolic, methacrylic, crotonic and oleic acid, especially those of maleic and fumaric acid.

The acyl radicals of carbocyclic acids are especially those of cyclohexanecarboxylic and benzoic acid that can be substituted, for example by a lower alkyl group, such as methyl, by an alkoxy group, such as methoxy or ethoxy, or by a carboxy group; of these, those of phthalic, isophthalic, terephthalic, cinnamic and toluic acid should be mentioned, and also those of 1- and 2-naphthoic acid and 1,2-cyclohexanedicarboxylic acid.

The acyl radicals of heterocyclic acids are, for example, those of furoic, thenoic, nicotinic, isonicotinic or picolinic acid.

A lower alkoxycarbonyl group is, for example, a methoxycarbonyl, ethoxycarbonyl, n-propoxycarbonyl, isopropoxycarbonyl, tert.-butoxycarbonyl or tert.-pentyloxycarbonyl group.

The optionally N-substituted carbamoyl groups are, for example, N-lower alkyl- or N,N-di-lower alkylcarbamoyl groups, such as N-methyl-, N-ethyl-, N,N-dimethyl- or N,N-diethyl-carbamoyl groups, or N-aryl-, N,N-di-aryl- or N-aryl-N-alkyl-carbamoyl groups, such as N-phenyl-, N,N-diphenyl- or N-phenyl-N-methyl- or -ethyl-carbamoyl, substituted or unsubstituted at the phenyl group.

A lower alkoxy group is, for example, a methoxy, ethoxy, n-propoxy, isopropoxy, n-butoxy, isobutoxy, sec.-butoxy, tert.-butoxy, n-pentyloxy or tert.-pentyloxy group.

A lower alkenyloxy group is, for example, a vinyloxy or allyloxy group.

A lower alkylenedioxy group is, for example, a methylenedioxy or ethylenedioxy group, or an isopropylidenedioxy group.

A cycloalkoxy group is, for example, a cyclopentyloxy, cyclohexyloxy or adamantyloxy group.

A phenyl-lower alkoxy group is, for example, a benzyloxy or a 1- or 2-phenylethoxy group.

A pyridyl-lower alkoxy group is, for example, the 2-, 3- or 4-pyridylmethoxy group.

A furyl-lower alkoxy group is, for example, the furfuryloxy group.

A thienyl-lower alkoxy group is, for example, the 2-thienyloxy group.

A lower alkylmercapto group is, for example, the methylmercapto or ethylmercapto group.

A phenyl-lower alkylmercapto group is, for example, the benzylmercapto or 1- or 2-phenylethylmercapto group.

A halogen is, for example, bromine, iodine or especially chlorine or fluorine.

A mono- or di-lower alkylamino group is, for example, the methylamino, dimethylamino, ethylamino or diethylamino group.

A lower alkyleneamino group optionally interrupted by hetero atoms is, for example, a pyrrolidinyl, piperidino, morpholino, thiamorpholino or 4-methylpiperazinyl group.

A lower alkanoylamino group is, for example, the acetylamino or propionylamino group.

The acyl radicals of mineral acids are, for example, those of sulphonic, sulphinic, sulphenic, phosphoric, boric or nitric acid.

The compounds of the invention comprising a radical containing salt-forming groups may also be in the form of salts.

Salts of compounds comprising a free carboxyl group are, for example, metal salts, especially salts of alkali metals, for example salts of sodium or potassium, and also salts of alkaline earth metals, for example salts of magnesium or calcium, and also salts of transition metals, for example salts of zinc, copper, iron, silver or mercury, or ammonium salts, for example those of ammonia or organic bases, such as tri-lower alkylamines, for example trimethylamine or triethylamine, especially non-toxic pharmaceutically acceptable salts of the above type.

The novel compounds comprising basic groups may also be in the form of acid addition salts, especially in the form of non-toxic pharmaceutically acceptable salts, for example with mineral acids, such as hydrochloric acid, hydrobromic acid, sulphuric acid or phosphoric acid, or with organic carboxylic or sulphonic acids, for example aliphatic, cycloaliphatic, cycloaliphatic-aliphatic, aromatic, araliphatic, heterocyclic or heterocyclic-aliphatic carboxylic or sulphonic acids, for example acetic, propionic, succinic, glycolic, lactic, malic, tartaric, citric, ascorbic, maleic, phenylacetic, benzoic, 4-aminobenzoic, anthranilic, 4-hydroxybenzoic, salicylic, aminosalicylic, embonic or nicotinic acid, and also methanesulphonic, ethanesulphonic, 2-hydroxyethanesulphonic, phenylsulphonic, 4-methylphenylsulphonic, naphthalenesulphonic, sulphanilic or cyclohexylsulphamic acid.

The novel compounds containing basic groups may be in the form of their quaternary ammonium compounds.

According to the invention, the compounds of the formula I and their pharmaceutically acceptable salts are used in pharmaceutical preparations having immunomodulating properties in doses necessary to bring about the desired effect in warm-blooded animals, these preparations containing the pharmacologically active substance alone or in admixture with another active substance of the same indication, together with at least one mineral or organic solid or liquid carrier that can be used in pharmacy and that is suitable for enteral or parenteral administration. The dosage of the active substance depends on the animal species, age and individual condition, and also on the method of administration. These pharmaceutical preparations are, for example, preferably in the form of dosage units, such as dragées, tablets, capsules, suppositories and ampoules.

Dosage units for peroral administration contain as the pharmacologically active substance up to 99%, preferably between 1 and 50%, of a compound of the formula I or of a pharmacologically active salt thereof. For the preparation of the dosasge units, this compound or salt is combined, for example, with a solid carrier or a carrier in the form of a powder, such as lactose, dextrose, sucrose, mannitol, sorbitol, cellulose and/or starches, such as maize starch, wheat starch, rice starch or arrowroot, or gelatin, if desired together with lubricants, for example magnesium or calcium stearate or polyethylene glycols, to form tablets or dragée, cores.

The dragée cores are then coated, for example with a concentrated sugar solution to which has been added, for example, gum arabic, talc and/or titanium oxide, or with a lacquer which is dissolved in a diluent or mixture of organic diluents that can be readily evaporated.

Examples of other dosage units according to the invention are gelatin capsules containing the active substance preferably in the form of a granulate, for example in admixture with diluents, such as maize starch, and/or lubricants, for example talc, magnesium stearate, and, if desired, stabilisers, such as sodium metabisulphite ($Na_2S_2O_5$) or ascorbic acid. In soft capsules the active substance is preferably dissolved or suspended in suitable liquids, such as a liquid polyethylene glycol, to which a stabiliser has optionally been added.

Dosage units according to the invention for rectal administration are especially suppositories which are composed especially of a mixture of a primary suppository base substance and the active substance. Examples of the primary suppository bases are natural or synthetic triglycerides, paraffin hydrocarbons, polyethylene glycols or higher alcohols. Capsules may also be used for rectal administration.

Ampoules for parenteral, especially intravenous, administration preferably contain the active substance or a salt of the active substance in solution, preferably at a concentration of from 0.5 to 10%.

The substances according to the present invention are administered in a quantity of from 1 to 1000 mg and preferably from 1 to 500 mg per dosage unit.

The active substance used in the present invention is especially a compound of the formula I in which R is an aliphatic, cycloaliphatic, cycloaliphatic-aliphatic, aromatic, aromatic-aliphatic, heterocyclic or heterocyclic-aliphatic hydrocarbon radical, or a radical of an aliphatic, cycloaliphatic, cycloaliphatic-aliphatic, aromatic, aromatic-aliphatic, heterocyclic or heterocyclic-aliphatic carboxylic acid, or a radical of an esterified or amidated carbonic acid, or a radical of an aliphatic, aromatic or aromatic-aliphatic sulphonic acid, or a radical of an inorganic acid having as the central atom a sulphur, phosphorus, boron or nitrogen atom, and the salts thereof.

The active substance used is especially a compound of the formula I in which R is an alkyl or alkenyl radical that is unsubstituted or substituted by hydroxy, lower alkanoyloxy, lower alkoxy, lower alkanoyl, nitrile, amino, mono- or di-lower alkylamino, lower alkyleneamino, oxa or aza-lower alkyleneamino, amido, or mono- or di-lower alkylamido groups or by halogen atoms; a cycloaliphatic radical containing from 3 to 6 ring carbon atoms that is unsubstituted or substituted by one or more hydroxy, lower alkoxy, lower alkyl, carboxy, oxo, lower alkanoylamino, mono- or di-lower alkylamino or lower alkoxycarbonyl groups; a cycloaliphatic-lower alkyl radical containing from 3 to 6 ring carbon atoms that is unsubstituted or substituted by at least one lower alkyl group; a phenyl or naphthyl radical that is unsubstituted or mono-, di- or tri-substituted by hydroxy, lower alkoxy, carboxy, lower alkoxycarbonyl, nitro, amino or mono- or di-lower alkylamino groups or by halogen atoms; a phenyl- or naphthyl-lower alkyl or alkenyl radical that is unsubstituted or mono-, di- or tri-substituted in the aromatic nucleus by hydroxy, lower alkoxy, carboxy, lower alkoxycarbonyl, lower alkanoyl, nitro, amino, mono- or di-lower alkylamino, amido, or mono- or di-lower alkylamido groups or by halogen atoms; a saturated or unsaturated aza-, thia-, oxa-, thiaza-, oxaza- or diaza-cyclic radical that may or may not be fused onto a phenyl nucleus, has from 2 to 7 carbon atoms in the heterocyclic nucleus and may be mono-, di- or poly-substituted by lower alkyl, hydroxy, lower alkoxy, nitro, carboxy, lower alkoxycarbonyl or lower alkanoyloxy groups; a heterocyclic-lower alkyl radical, the hetero ring of which is one of those described above; or a radical of a lower alkanecarboxylic, lower alkenecarboxylic, lower alkanedicarboxylic lower alkenedicarboxylic acid or cyclolower alkanecarboxylic acid, which is unsubstituted or substituted by one or more hydroxy, lower alkoxy, carboxy, lower alkoxycarbonyl, lower alkyl, lower alkanoyl or oxo groups or by halogen atoms; a benzoyl or naphthoyl radical optionally substituted by hydroxy, lower alkoxy, lower alkanoyloxy, carboxy, lower alkoxycarboxyl, nitro or amino groups or by halogen atoms; a radical of a phenyl- or naphthyl-lower alkanoic acid that is unsubstituted or substituted in the aromatic moiety by one or more hydroxy, lower alkoxy, carboxy, lower alkoxycarbonyl, lower alkanoyl, lower alkanoyloxy, nitro, amino or mono- or di-lower alkylamino groups or by halogen atoms; a radical of a saturated or unsaturated aza-, thia-, oxa-, thiaza-, oxaza- or diaza-cyclic acid that can be fused onto a phenyl group; a lower alkoxycarbonyl radical; a phenoxycarbonyl radical; a carbamoyl radical optionally mono- or di-substituted by lower alkyl radicals or phenyl or benzyl radicals optionally substituted at the phenyl nucleus by one or more hydroxy or lower alkoxy groups or by halogen atoms; a radical of a lower alkylsulphonic or phenylsulphonic acid optionally substituted by one or more lower alkyl or lower alkoxy groups or by halogen atoms; or a radical of a phosphoric acid that is unsubstituted or esterified by one or two lower alkyl groups or by one or two optionally substituted phenyl groups; and the salts thereof.

The active substance used is more especially a compound of the formula I in which R is a lower alkyl radical that is unsubstituted or substituted by one, two or several hydroxy, lower alkoxy, lower alkanoyloxy, carboxy, nitrile, lower alkanoyl, amino, mono- or di-lower alkylamino, lower alkyleneamino or oxa- or aza-lower alkyleneamino groups or by chlorine or fluorine atoms; a cycloaliphatic radical containing 5 or 6 ring carbon atoms that is unsubstituted or substituted by lower alkyl, hydroxy, lower alkoxy, carboxy, lower alkoxycarbonyl, amino or mono- or di-lower alkylamino groups; a cycloaliphatic alkyl radical having from 1 to 4 carbon atoms and the ring of which contains 5 or 6 carbon atoms and that may be substituted by at least one alkyl group having from 1 to 4 carbon atoms; a phenyl radical that is unsubstituted or mono-, di- or tri-substituted by hydroxy, alkoxy containing from 1 to 4 carbon atoms, carboxy, nitro, amino or mono- or di-$(C_1-C_4)$-alkylamino or by chlorine or fluorine atoms; a benzyl, phenylethyl or phenylpropyl radical that is unsubstituted or mono-, di- or tri-substituted in the phenyl nucleus by hydroxy, alkoxy containing from 1 to 4 carbon atoms, carboxy, alkoxycarbonyl having from 1 to 4 carbon atoms, nitro, amino or mono- or di-$(C_1-C_4)$-alkylamino, or by chlorine or fluorine atoms; a tetrahydropyranyl, pyridyl, quinolinyl or pyrimidyl radical optionally substituted by one or more nitro, amino or hydroxy groups; a radical of an alkanecarboxylic acid containing from 3 to 18 carbon atoms that is unsubstituted or substituted by one or more of the groups hydroxy, carboxy, alkoxycarbonyl having from 1 to 5 carbon atoms, alkyl having from 1 to 5 carbon atoms, amino or mono- or di-$(C_1-C_4)$-alkylamino or by chlorine or fluorine atoms; a radical of a cycloalkanecarboxylic acid having from 3 to 6 ring carbon atoms that is unsubstituted or substituted by one or more of the groups hydroxy, carboxy, lower alkoxycarbonyl, amino or mono- or di-$(C_1-C_4)$-alkylamino or by chlorine or fluorine atoms; a radical of a cycloalkylalkanoic acid, the aliphatic chain having from 1 to 4 carbon atoms and the ring having from 3 to 6 carbon atoms; a benzoyl radical that is unsubstituted or mono-, di- or tri-substituted by the groups hydroxy, alkoxy containing from 1 to 4 carbon atoms, carboxy, alkoxycarbonyl containing from 1 to 4 carbon atoms, alkanoyl containing from 1 to 4 carbon atoms, alkanoyloxy having from 1 to 4 carbon atoms, nitro, amino or mono- or di-$(C_1-C_4)$-alkylamino or by chlorine or fluorine atoms; a radical of a phenylalkanoic acid the aliphatic chain of which contains from 1 to 4 carbon atoms and the phenyl group of which may be substituted as indicated for the benzoyl group; a radical of a nicotinic or isonicotinic acid; an alkoxycarbonyl radical having from 1 to 4 carbon atoms in the alkyl moiety; a carbamoyl radical optionally mono- or di-substituted by alkyl groups having from 1 to 4 carbon atoms or phenyl groups that are unsubstituted or substituted by hydroxy, methoxy or ethoxy groups or by chlorine or fluorine atoms; or a radical of an unsubstituted or mono- or di-methylated, -ethylated or -phenylated phosphoric acid; and the salts thereof.

The present invention concerns, as the active substance, especially compounds of the formula I in which R is a lower alkyl radical that is unsubstituted or substituted by one or two of the groups hydroxy, alkoxy having from 1 to 4 carbon atoms, carboxy, alkanoyloxy containing from 1 to 4 carbon atoms, amino, mono- or di-$(C_1-C_4)$-alkylamino or nitrile; a cycloaliphatic radical containing 5 or 6 ring carbon atoms that is unsubstituted or substituted by one or two of the groups hydroxy, alkoxy containing from 1 to 4 carbon atoms, carboxy, alkanoyloxy containing from 1 to 4 carbon atoms, amino or di-lower alkylamino; a cycloalkylalkyl radical the alkyl moiety of which comprises from 1 to 4 carbon atoms and the ring of which contains 5 or 6 carbon atoms; a phenyl radical that is unsubstituted or mono-, di- or tri-substituted by hydroxy, methoxy, ethoxy, propoxy, amino or nitro groups; a benzyl, phenylethyl or phenylpropyl radical that is unsubstituted or mono- or di-substituted at the phenyl nucleus by one or two of the groups hydroxy, methoxy, ethoxy, propoxy, carboxy, alkoxycarbonyl containing from 1 to 4 carbon atoms, nitro, amino or mono- or di-($C_1$-C)-alkylamino or by chlorine or fluorine atoms; a tetrahydropyranyl radical; a pyridyl radical that is unsubstituted or substituted by a nitro, amino or hydroxy group; a radical of an alkanecarboxylic acid containing from 3 to 18 carbon atoms that is unsubstituted or substituted by one or more of the groups hydroxy, carboxy, alkoxycarbonyl containing from 1 to 6 carbon atoms, alkanoyl containing from 1 to 5 carbon atoms, amino or mono- or di-($C_1$-$C_4$)-alkylamino or by chlorine or fluorine atoms; a radical of a cycloalkanecarboxylic acid containing 5 or 6 ring carbon atoms that is unsubstituted or substituted by one, two or three of the groups hydroxy, carboxy, alkoxycarbonyl containing from 1 to 4 carbon atoms, amino or mono-or di-($C_1$-$C_4$)-alkylamino or by chlorine or fluorine atoms; a radical of a cycloalkylalkanoic acid the alkyl chain of which contains from 2 to 4 carbon atoms and the cycloalkane moiety of which contains 5 or 6 ring carbon atoms; a benzoyl radical that is unsubstituted or mono-, di- or tri-substituted by the groups hydroxy, alkoxy containing from 1 to 4 carbon atoms, carboxy, alkoxycarbonyl containing from 1 to 4 carbon atoms, alkanoyl containing from 1 to 4 carbon atoms, alkanoyloxy containing from 1 to 4 carbon atoms, nitro, amino or mono- or di-($C_1$-$C_4$)-alkylamino or by chlorine or fluorine atoms; a radical of a phenylalkanoic acid the aliphatic chain of which comprises from 1 to 4 carbon atoms and the phenyl group of which is unsubstituted or substituted by one or two of the groups hydroxy, alkoxy containing from 1 to 4 carbon atoms, amino, carboxy, alkoxycarbonyl containing from 1 to 4 carbon atoms, alkanoyl containing from 1 to 4 carbon atoms, alkanoyloxy containing from 1 to 4 carbon atoms or by chlorine or fluorine atoms; a radical of a nicotinic or isonicotinic acid; an alkoxycarbonyl radical having from 1 to 4 carbon atoms; a carbamoyl radical optionally mono-substituted by alkyl groups containing from 1 to 4 carbon atoms or phenyl; or a radical of an unsubstituted phosphoric acid or of a dimethyl-, diethyl- or monohydroxyphenyl-phosphoric acid.

The present invention concerns, as the active substance, more especially compounds of the formula I in which R is a lower alkyl radical that is unsubstituted or substituted by hydroxy, alkoxyamino having from 1 to 4 carbon atoms or nitrile; a cycloalkylalkyl radical the alkyl moiety of which comprises from 1 to 4 carbon atoms and the ring of which contains 5 or 6 carbon atoms; an unsubstituted benzyl, phenylethyl or phenylpropyl radical; a tetrahydropyranyl radical; a radical of an alkanecarboxylic acid containing from 3 to 18 carbon atoms that is unsubstituted or substituted by hydroxy or carboxy; a radical of a cycloalkanecarboxylic acid containing 5 or 6 ring carbon atoms that is unsubstituted or substituted by a benzyl radical that is unsubstituted or mono-, di- or tri-substituted by the groups hydroxy, carboxy, alkoxycarbonyl containing from 1 to 4 carbon atoms or alkanoyloxy containing from 1 to 4 carbon atoms or by chlorine or fluorine atoms; a radical of a phenylalkanoic acid the aliphatic chain of which comprises from 1 to 4 carbon atoms and the phenyl group of which is unsubstituted; a radical of a nicotinic or isonicotinic acid; an alkoxycarbonyl radical having from 1 to 4 carbon atoms; a carbamoyl radical mono-substituted by alkyl groups containing from 1 to 4 carbon atoms or phenyl; or a radical of an unsubstituted phosphoric acid or a dimethyl-, diethyl- or monohydroxyphenyl-phosphoric acid.

As active substance, there should be noted especially compounds of the formula I in which R is a radical of an alkanecarboxylic acid containing from 3 to 18 carbon atoms that is unsubstituted or substituted by hydroxy or carboxy; a radical of a cycloalkanecarboxylic acid containing 5 or 6 ring carbon atoms that is unsubstituted or substituted by a carboxy group, a benzoyl group that is unsubstituted or mono-, di- or tri-substituted by the groups hydroxy, alkoxy containing from 1 to 4 carbon atoms, carboxy, alkoxycarbonyl containing from 1 to 4 carbon atoms or alkanoyloxy containing from 1 to 4 carbon atoms or by chlorine or fluorine atoms; a radical of a phenylalkanoic acid the aliphatic chain of which comprises from 1 to 4 carbon atoms and the phenyl group of which is unsubstituted; a radical of a nicotinic or isonicotinic acid; an alkoxycarbonyl radical having from 1 to 4 carbon atoms; a carbamoyl radical mono-substituted by alkyl groups containing from 1 to 4 carbon atoms or phenyl; or a radical of an unsubstituted phosphoric acid or of a dimethyl-, diethyl- or monohydroxyphenyl-phosphoric acid.

The invention is described in more detail in the non-limiting Examples which follow in which the temperatures are given in degrees Centigrade.

EXAMPLE 1

In order to obtain 15,000 tablets 3.75 kg of 3-0-palmitoyl-(+)-cyanidan-3-ol are mixed with 0.18 kg of silicon dioxide and 0.075 kg of corn starch. After granulation under moist conditions with 0.12 kg of corn starch and 0.225 kg of gelatin, the dry granulate is mixed with 0.03 kg of magnesium stearate. 15,000 tablets are then manufactured in a rotary machine. One tablet weighs 295 mg and contains 250 mg of active substance.

EXAMPLE 2

The tablets according to Example 1 are then coated with a solution based on methylene chloride containing 1.35 kg of polyvinylpyrrolidone, 6.3 kg of methylcellulose, 1.4 kg of colourant and 3.24 kg of gum lacquer.

EXAMPLE 3

In order to obtain sugar dragees, the tablets according to Example 1 are coated with a concentrated syrup containing 20.8 kg of saccharose, 0.3 kg of shellac, 0.5 kg of gum arabic and 0.08 kg of colourant. After drying, the dragées each weigh 400 mg.

EXAMPLE 4

In order to obtain 1000 capsules containing 500 mg of 3-0-benzoyl-(+)-cyanidan-3-ol, 500 g of 3-0-benzoyl-(+)-cyanidan-3-ol are mixed with 8 g of stearin powder and 1 g of magnesium stearate. The mixture is graded by passing it through netting of 1 mm mesh diameter and then filled into 1000 hard gelatin capsules, size No. 0.

EXAMPLE 5

Granulation under moist aqueous conditions is carried out with 1 kg of 3-0-heptyl-(+)-cyanidan-3-ol and 2 kg of mannitol. After drying and grading, the granulate is mixed with 100 g of fruit flavouring and filled into 1000 sachets. Each sachet contains 1 g of active substance.

EXAMPLE 6

2 kg of 3-0-methoxymethyl-(+)-cyanidan-3-ol are dissolved in 6.0 kg of propylene glycol. The mixture is introduced into a solution containing 30.0 kg of saccharose, 3.0 kg of sorbitol, 0.06 kg of sodium bisulphite, 0.06 kg of sodium benzoate and 73 kg of distilled water. The syrup so obtained contains 2% of active substance.

EXAMPLE 7

75 g of 3-0-methyl-(+)-catechol, 1.6 g of bisodium phosphate and 34.5 g of sodium chloride are dissolved in 4.9 kg of twice-distilled water. After sterile filtration through a membrane filter (pore diameter: 0.2 μm), the solution is filled under nitrogen into 1000 sterile 5 ml ampoules. Each ampoule contains 75 mg of active substance in the form of a 1.5% aqueous solution.

EXAMPLE 8

A suppository base is prepared containing 0.3 kg of 3-0-acetylsalicylyl-(+)-cyanidan-3-ol and 1.7 kg of fatty acid triglyceride ether and 1000 suppositories are cast each containing 300 mg of active substance.

EXAMPLE 9

In order to obtain an ointment containing 5% active substance, 5 g of 3-0-dodecyl-(+)-cyanidan-3-ol are mixed with 10 g of propylene glycol and 10 g of water and then emulsified in the melted fatty phase containing 65 g of vaseline and 10 g of cetylstearylic alcohol.

We claim:

1. A method of stimulating the immune response of a mammal, in a mammal requiring such stimulation, comprising administering to said mammal by enteral or parenteral administration an immune response stimulating effective daily amount of a 3-0-substituted-(+)-cyanidan-3-ol of the formula

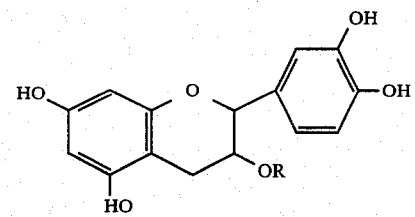

in which R is a radical of an alkanecarboxylic acid containing from 3 to 18 carbon atoms.

2. A method of stimulating the immune response of a mammal, in a mammal requiring such stimulation, comprising administering to said mammal by enteral or parenteral administration an immune response stimulating effective daily amount of 3-0-palmitoyl-(+)-cyanidan-3-ol.

* * * * *